United States Patent [19]
Vazquez, Jr. et al.

[11] Patent Number: 5,833,640
[45] Date of Patent: Nov. 10, 1998

[54] ANKLE AND FOOT SUPPORT SYSTEM

[76] Inventors: Roderick M. Vazquez, Jr., P.O. Box 3471, Auburn, Ala. 36831-3471;
Kenneth W. Bramlett, 1744 Oxmoor Rd. Suite 200, Homewood, Ala. 35209

[21] Appl. No.: 798,914

[22] Filed: Feb. 12, 1997

[51] Int. Cl.$^6$ .................................................. A61F 5/00
[52] U.S. Cl. .............................. 602/27; 602/63; 602/65
[58] Field of Search ................................ 602/23, 27–29, 602/61–63, 65, 66; 128/882

*Primary Examiner*—Linda C. Dvorak
*Attorney, Agent, or Firm*—Doug Murdock

[57] ABSTRACT

An ankle and foot support brace is described which is made of three components; an inner slide-on sleeve, a plantar cushion, and an outer mono-unit strapping system. The sleeve is very thin at a thickness of about one-thirty-seconds of an inch. The sleeve is made of a stretchable resilient material such as Spandex. The plantar cushion may be removable or permanently attached to the brace and can further be personalized in its makeup to form a therapeutic orthotic. The mono-unit strapping system is also thin, made of strong resilient composite, and having a thickness commensurate with the sleeve and includes two heel lock straps, two stirrup straps, and two figure eight straps. The lateral stirrup includes two locking straps.

9 Claims, 20 Drawing Sheets

ANKLE AND FOOT SUPPORT SYSTEM

FIELD OF INVENTION

This invention relates to ankle and foot support braces. More particularly, this invention relates to such braces that are useful in providing orthotic support for aiding the recovery of injured ankles and feet, and for protecting the wearer against injuries commonly sustained during sports activities.

BACKGROUND

The field of ankle braces has many examples of inventions the designs of which are intended to provide one manner of support or another to the ankle and foot bones, ligaments, and musculature. However, of the numerous inventions, no single design has solved the multiple problems often observed with ankle/foot injury. Likewise, no single design has solved the practical requirements of athletes who desire to wear such bracing during active engagement in their chosen sport. Accordingly, a long felt need has existed in this art for an ankle/foot bracing system which is capable of serving the needs of physicians who wish to provide exacting support for injured bone, ligament, and musculature, and athletes who wish to protect themselves from specific ankle and foot injuries.

The advent of lightweight high strength synthetic material technology has allowed for the design of the present invention for highly versatile pre and post injury use. Moreover, the present invention has specific elements which will aid the protection, support, and rehabilitation of specific ligaments and muscles making up the ankle and foot musculature. The benefit provided by the present invention may be best understood by examining and delineating the marked differences and limitations of prior ankle and foot brace designs the following of which are exemplary.

U.S. Pat. No. 4,166,460 entitled ANKLE PROTECTOR, by L. T. Applegate, provides an ankle brace the primary intent of which is to provide lateral rigidity to the ankle and immobilization support to the heal and instep. This invention allows the ankle to be moved only in an up and down rotation commensurate with normal walking. The shape and design of the semi-rigid heal cup, the semi rigid vertical support stays which are anchored to the inside of the elastic stocking, and the straps attached to the bottom of the instep section of the brace, make wearing the device during sports activities uncomfortable and highly impractical. Moreover, since the stocking portion of the invention is elastic, lateral support must come solely from the vertical stays and wrapping of the straps. The Applegate invention is therefore predominantly a post injury device meant to be used to allow injuries to heal. Notably, the disclosure provides that inward and outward bending of the ankle is inhibited and the straps are as much as three and one half feet in length designed for multiple encirclement of the instep and ankle. The attributes of the Applegate invention are vastly different from both the design and concept of the present invention which desires to allow for manipulation of inward and outward bending of specific ankle ligament groups and does not require multiple encirclement of straps about the instep.

Another sleeve like ankle brace is disclosed in U.S. Pat. No. 4,844,058 entitled BIOMECHANICAL ANKLE BRACE, by W. D. Vogelbach. Like the Applegate invention, this device is contemplated for use post injury and requires the patient's ankle to be encased in plaster of Paris in order to obtain a mold of the ankle and foot so that the device can be crafted to fit the individual user. Although Vogelbach discloses placing strap supports in biomechanically correct positions, the overall design does not accomplish the exacting and versatile operative capability of the present invention. The Vogelbach design contemplates an elastic sleeve, like the Applegate device, and has straps sewn to the bottom of the sleeve, a location that has three main impractical effects. First, the position of sewing creates texture on the bottom of the device which adversely affects comfort to the sole of the foot. Second, the position of the anchoring of the straps on the sole of the sleeve does not achieve the natural support obtained with the strap positioning of the present invention. The positioning of strapping across the bottom or plantar area specifically causes the upward tension created by upward force on the straps to initiate around and about the bottom of the foot. The force thus realized is not comparable to natural tendon forces which initiate from the lateral portions of the foot. The present invention, in contrast, is designed to initiate tension on the foot from lateral positions and directions so as to apply forces which are more anatomically correct. Third, the straps are bulky and cause impracticality of active wear use. The Vogelbach device additionally contemplates securing the sleeve to the leg and foot by secondary bands which tighten about the calf and foot. Such banding of straps again make the device impractical for pre-injury use during active movement.

Similar to the Vogelbach device, U.S. Pat. No. 4,962,768 entitled STIRRUP-LOCK ANKLE SUPPORT, by L. T. Stromgren, discloses a sleeve like device having broad straps attached to the Achilles tendon area of the sleeve and are configured to be wrapped around the bottom of the foot and around the ankle. Additionally, the straps are stretchable along their length. The present invention by contrast does not contemplate wrapping of straps in any manner beneath the foot. Moreover, because of the exacting nature of the strap's function, the present invention has relatively inelastic strapping. There is no need for compression wrapping as is the case with Stromgren's device.

In U.S. Pat. No. 4,878,504 entitled ANKLE BRACE WITH COMPRESSION STRAPS, by R. E. Nelson, a lace-up ankle brace is disclosed which purports to provide compression support by restricting extension of the foot downward and preventing abnormal twisting of the ankle. This brace further is intended to be worn during sports activities. However, like the designs discussed above, this device is unable to provide the degree of support actually necessary in rigorous activity. The sleeve is made of relatively inelastic canvas or vinyl. Since the sleeve completely covers the ankles, even with padding, the pressure caused by the straps against the thickness of the canvas will make wearing the sleeve uncomfortable during active wear. Moreover, this device has only two straps which, in comparison to athletic tape, is considerably less adequate in inhibiting lateral or rotational movement of the ankle. The current invention in contrast has a much thinner sleeve that will accommodate comfort and the wearing of athletic foot gear, and has strapping that functions in a highly versatile fashion to support various ligament groups as desired by the wearer.

Another device which is similar to the Nelson invention is disclosed in U.S. Pat. No. 5,016,623 entitled ANKLE SUPPORT, by D. W. Krahenbuhl. This device comprises a laced sleeve having a single strap. Importantly, one object of the present invention is to provide an ankle support which is practical for sports use. The Krahenbuhl device, like the Nelson brace, is inadequate in this regard because of its bulk. The lacing which extends along the length of the wearer's foot interferes with athletic foot gear. Moreover, the single strap is wholly in adequate to provide exacting support necessary for athletic activities.

Yet another device, U.S. Pat. No. 5,099,860 entitled ORTHOTIC DEVICE FOR THE DYNAMIC TREATMENT OF TEARING OR STRAINING OF THE LIGAMENTS OF THE LATERAL ANKLE, by M. Amrein, discloses a sleeve like brace made of cloth and contains essential splints which provide lateral support. Again, this device differs from the present invention in numerous ways such as the use of splints, the method of attaching straps, and the manner of wrapping such straps.

Still other devices have been disclosed (U.S. Pat. No. 4,729,370 by Kallassy, U.S. Pat. No. 5,330,419by Toronto, U.S. Pat. No. 5,472,414 by Detty, U.S. Pat. No. 5,445,603 by Wilkerson, and U.S. Pat. No. 5,501,659 by Morris ) all of which, though providing support to ankle musculature, are essentially post injury devices having no practical utility for use by athletes during sporting activity.

Notwithstanding the various designs of prior ankle braces, there has not yet been described a brace that is as effective in providing support as is presently obtained from athletic wrapping tape or that has the degree of practical utility necessary for use by athletes during sporing activities. The primary reason that prior designs have not provided the necessary degree of usefulness required in strenuous sports, is that materials contemplated for construction of prior braces are bulky and the designs of such prior braces create a bulky mass about the foot and ankle. Thus, the typical brace is useful only for post injury support. In contrast, the present invention solves several of the most important aspects of ankle and foot bracing which are necessary, if not critical to practical functionality in pre injury application.

SUMMARY OF THE INVENTION

The instant invention contemplates a lower leg, ankle, and foot support designed for use in preventing, treating, and rehabilitating injuries to ligaments and musculature of the leg, ankle, and foot. Support of the leg, foot, and ankle are provided by a combination of elements making up the brace including an outer mono-unit strapping system, a foot sole or plantar padding, and an inner slide-on sleeve. The strapping system and sleeve are constructed of materials newly introduced to the art of appendage bracing that is both thin and durable. For the sleeve, this new material has a long chain synthetic polymer with 85% poly urethane commonly known in the art as LYCRA or Spandex. The sleeve is a composite that is three layered and is elastic and breathable yet water proof. The inner and outer layers are the LYCRA/Spandex while the third layer comprises a thermoplastic film sandwiched in between. This composite material is also found under commercial names of BIOSKIN and EPX. The strapping system is a composite of thermoset or thermoplastic having variable rigidity as is well understood in the art, such material being a KEVLAR like fiberous composite of epoxyresin. The use of these materials will allow for the ankle sleeve and strapping system to be as thin as approximately one-thirty-second of an inch in thickness. The thickness may also be stated as 1 mil, a measurement understood in the textile industry. Moreover, due to the elasticity of this material, there will be increased proprioception of the leg, ankle, and foot, as well as proprioceptive training of the ankle. Such training is important to rehabilitation of injured tissue as the receptors of the muscles and tendons will learn when they have reached the limit of their capacity for stretching and, due to such training, eventually allow use of the appendage without a brace.

The slide-on sleeve component provides a measurable advance over prior designs in a number of respects. First, the sleeve is made of extremely thin yet exceptionally strong material. This feature makes possible for the first time a brace that is truly thin enough to be used directly with unmodified sports foot gear.

Secondly, a preferred embodiment contemplates a plantar surface making up the bottom of the sleeve extending from the heel to the distal end of the toes. In another embodiment, the plantar surface stops at the base of the toes just in front of the ball of the foot. The sleeve is designed so as to avoid stitching on the plantar surface thereby eliminating the possibility of irregularities which would otherwise be felt by the foot and which would cause discomfort during strenuous athletic activity. In a preferred embodiment, the toes and heal of the wearer are exposed, whether or not the sole extends to the distill end of the toes. This feature helps keep unnecessary bulk to a minimum as well as provide aeration and additional comfort to the athlete. In yet another embodiment, the heel is covered by the composite LYCRA or Spandex material confluent with the rest of the sleeve while the toes are covered by a breathable mesh allowing the toes and foot to be aerated and have additional protection from extraneous matter.

Third, the sleeve is kept firmly in place on the foot and ankle without the possibility of slipping because of the form-fitting nature of the sleeve about the arch of the foot, the anchoring of the heal in juxtaposition with a rain drop shaped heal slot opening at the heel cup, the stretchable quality of the composite material making up the dorsal arch area and posterior leg area above the heel slot, and the lace-up configuration from above the foot and ankle joints to the top of the sleeve. The lacing is a marked advantage in the particular format of the instant invention. All prior braces that lace initiate the lacing from a position near the toes. Such placement caused the laces to be inside the wearer's shoe adding extra bulk with decreased comfort. In contrast, the instant invention contemplates lacing designed to begin at the distal end of the lower leg above the ankle joint and outside the athlete's shoe. Additionally, the tongue of the sleeve is also attached above the ankle joint so that the tongue need not extend into the shoe. In a preferred embodiment, the tongue is wider at the top than at the bottom and has a plurality of looped lace keepers which act to guide the laces between the eyelets and also keep the tongue in proper position. The rain drop shaped heel cup allows the Calcaneal (Achilles) tendon and heel to be free from obstructions which may either cause irritation of the heel and Achilles tendon or interfere with a firm fit between the wearer's heel and shoe. Comfort and a firm fit are further advanced by use of a very thin elastic material on the area of the sleeve covering the top of the foot and the area covering the length of leg from above the Achilles tendon to the top of the brace. This stretch material further helps the sleeve fit snugly around the lower leg and helps keep the material of the sleeve at the front of the brace along the tongue attachment junction from wrinkling or scrunching. This thin stretch material is a variation of the main sleeve material but has a weave that allows it to have greater elastic qualities.

A further embodiment of the invention contemplates that stitching of the material making up the sleeve will be on the dorsal and posterior surfaces of the brace to reduce tension that would be present in the material fabric if such stitching were located on the plantar surface. The placement of the stitching on dorsal and posterior surfaces further avoids the possibility of cramping and discomfort that the wearer would experience if stitching were located along the sole creating an irregular surface.

Fourth, the top of the sleeve contemplates a shape conforming to the curvature of the gastrocnemius (calf muscle). Thus, the sleeve and lacing may project up the shin of the lower leg yet not interfere or cause discomfort to the wearer's calf muscles.

The second component, the plantar cushion, is connected to the underside of the sleeve's plantar surface and may include several possible configurations. The preferred embodiment contemplates a plantar cushion extending from under the heel to the distal end of the toes. Since the invention contemplates custom fitting to meet a wearer's personal needs, the plantar cushion may be designed as an orthotic having a rigidity or pliability commensurate with the individual's specific requirements in treatment of foot, ankle, and leg disorders. Thus, the invention contemplates a sole cushioned by air, gel, or foam. Another embodiment contemplates providing a sole with an instep. Yet another embodiment contemplates a sole having an air filled bladder. Since the sleeve may be designed with a plantar surface that ends just behind the toes, other embodiments of the invention contemplate a plantar padding having a length providing support from the heel to just behind the toes.

The third component of the present invention contemplates a strapping system of which a preferred embodiment is a mono-unit system composed of composite material that is both thin and strong. In the preferred embodiment, the material is thermoset or thermoplastic composite KEVLAR. The mono-unit system is designed for uniform fit and comfort as well as versatility in providing a range of support from complete immobilization of the foot to support with variable degrees of flexibility for active wear use. Although the material of the strapping system can be any desirable thickness, a preferred embodiment contemplates a mono-unit strapping system at least one-thirty-second of an inch in thickness. The thickness can also be 1-mil.

The mono-unit consists of one piece of material cut to include a plantar surface and a plurality of straps. The mono-unit design feature is a marked advance over prior brace strapping designs because several functions are performed. First, such design is an advancement over prior brace designs in that there is no need for additional stitching that would otherwise be necessary for individual straps. Second, the mono-unit system includes dual stirrup straps which provide support on both medial and lateral sides of the ankle preventing direct rolling or flexion of the ankle joint. Third, the point of initiation of tensional forces from strapping is from the sides of the brace above the plantar area allowing for more natural tensional forces. Fourth, the position and direction of force of the straps is designed to provide optimal imitation of natural tensional forces provided by tendons and ligaments of the foot musculature.

A preferred embodiment of the invention contemplates that the stirrups will begin slightly superior to the malleolus and extend upwards to a fixed position on the lower leg by use of VELCRO attachment means. For one embodiment, the lateral stirrup has two lock down straps, one leading anterior and the other towards the posterior of the brace. These lock down straps are at a slightly greater angle than perpendicular with the stirrup and are intended to be wrapped around the brace to the medial side for attachment across and on top of the medial stirrup strap. Another preferred embodiment contemplates dual figure eight straps designed to prevent or reduce inversion, eversion, and plantar flexion. The amount of support provided by these straps is determined by the desired use of the brace, the predetermined thickness of strapping, and the tension placed on the individual straps as they are anchored to the sleeve. The figure eight straps begin on the medial and lateral surfaces between the dorsal and plantar surfaces of the brace. When strapped, the figure eight straps will cross on the anterior surface and wrap around to posterior surface to end on the same side as they originated. The medial figure eight strap may also provide support to the medial longitudinal arch by supporting the Tibialis Posterior tendon and the spring ligament. A preferred embodiment contemplates use of VELCRO for securing the straps in place.

Yet another preferred embodiment contemplates dual heel locking straps which have their origin directly posterior and inferior to the origin of the stirrups, both medially and laterally. The heel locking straps extend upwards and wrap around the opposite surface of the brace. The heel locking straps produce two major functions, the locking of the calcaneus and talus into the ankle mortise, and the preventing of over stretching or tearing of the Achilles tendon. The heel straps provide a special benefit to the user in that they can aid greatly the prevention of serious career ending injuries.

Another preferred embodiment of the invention contemplates attachment of the sleeve, plantar cushion, and mono-unit strapping together by either glue or stitching or both. One embodiment contemplates stitching along the lateral and medial sides of the sleeve and mono-unit between the malleolus and the toe end of the brace above the plantar surface. A second embodiment contemplates stitching around the perimeter of the plantar surfaces of the sleeve and mono-unit such that a pocket is formed which may accommodate the plantar cushion. Such stitching avoids using midline seems on the plantar surface. The stitching may, if desired, anchor the plantar cushion to the sleeve and mono-unit strapping system.

A further embodiment of the invention contemplates the presence of a semipermanent seam between the sleeve and strapping unit running across the posterior of the heel cup plantar area such that the plantar cushion may be removed and replaced as desired.

BRIEF DESCRIPTION OF THE DRAWINGS

The foregoing and other objects or features and advantages of the invention will be made apparent from the following detailed description of the preferred embodiments of the invention and from the drawings in which.

DETAILED DESCRIPTION

Figure 1:
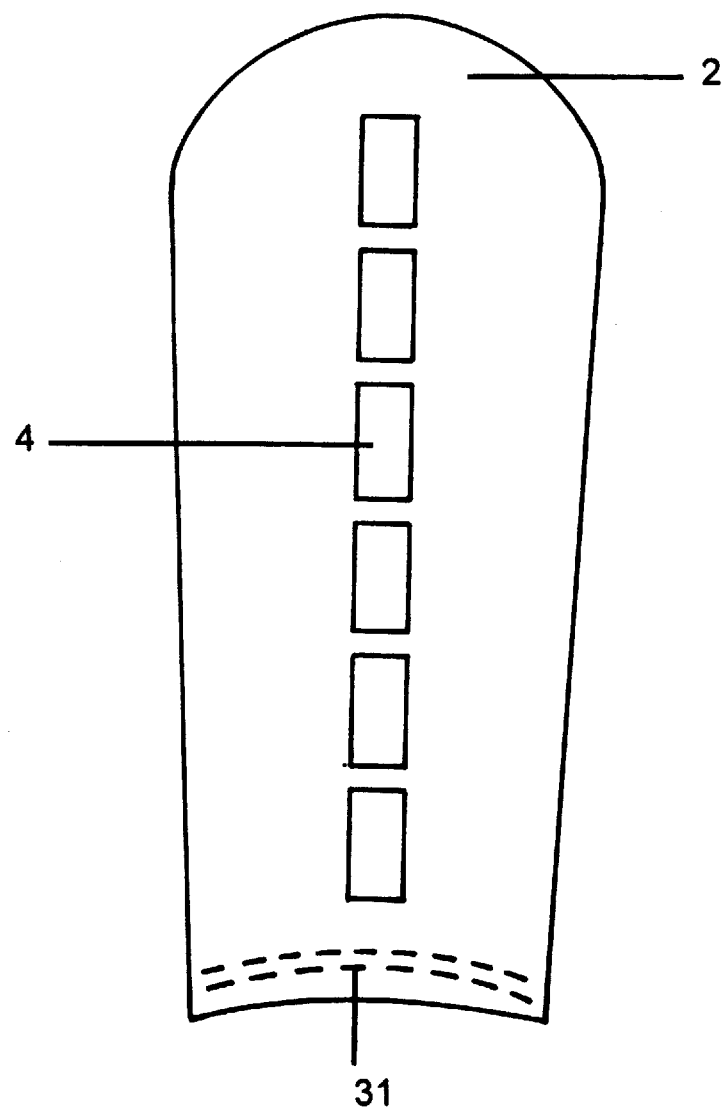
FIG. 1 is a frontal view of the tongue of the sleeve.
Figure 2:
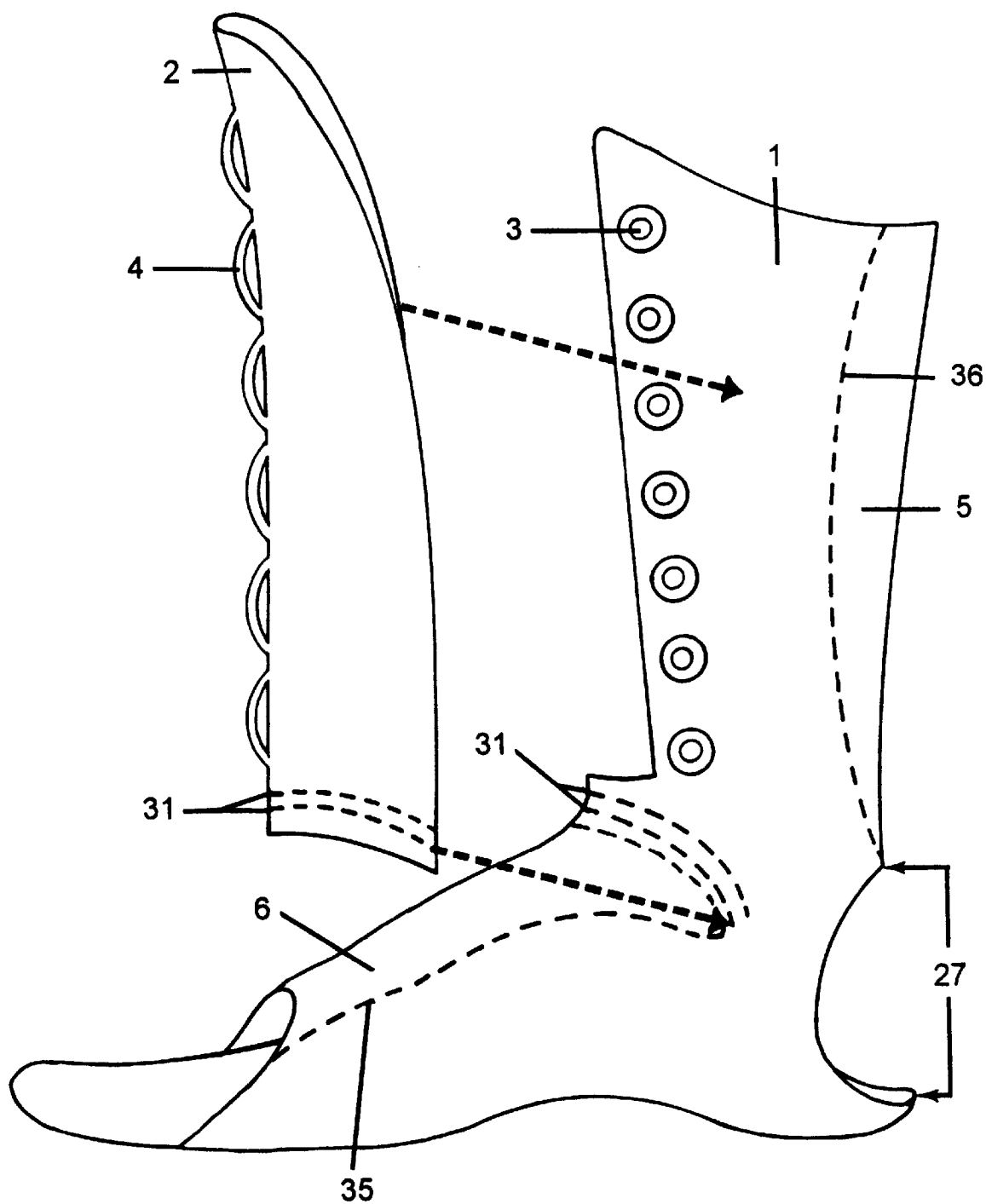
FIG. 2 is a side view of the sleeve and tongue.
Figure 3:
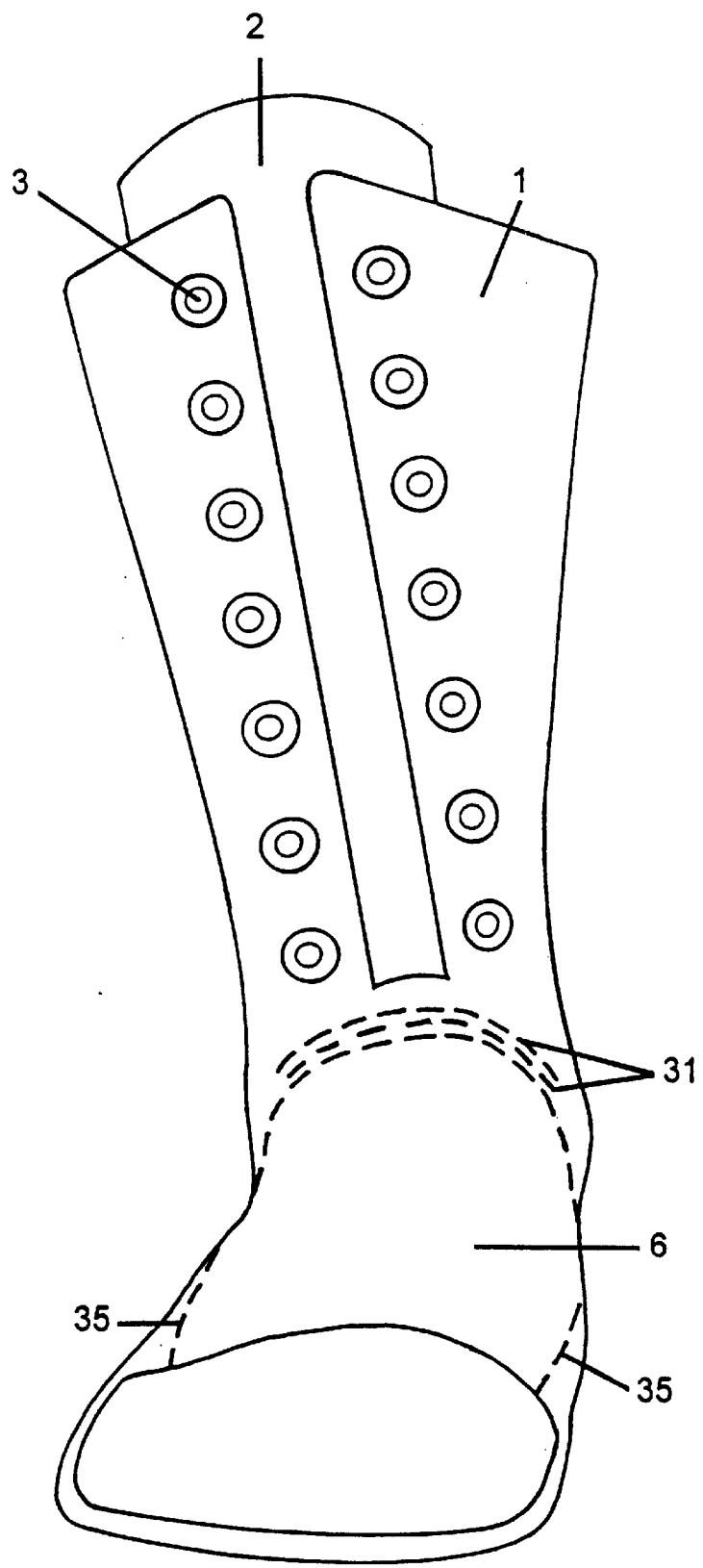
FIG. 3 is a frontal view of the sleeve.
Figure 4:
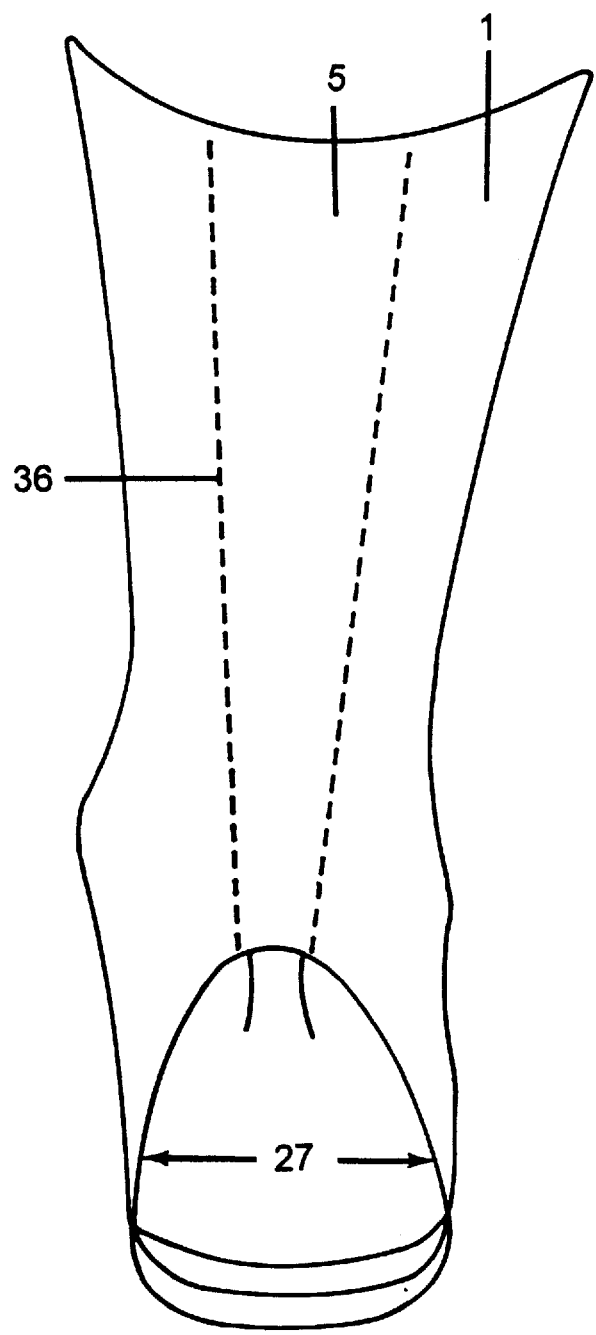
FIG. 4 is a rear view of the sleeve.

Referring now to FIGS. 1 through 4, inner sleeve 1 and sleeve tongue 2 are shown. The sleeve 1 supports a plurality of lace eyelets 3 positioned vertically along the leading edge of the leg portion of the sleeve 1. Tongue 2 is attached to the sleeve 1 at stitching lines 31. Tongue 2 may further support lace keeper loops 4. The lower posterior area of the sleeve 1 has a tear drop shaped heel cup seat or slot 27 which allows the wearer's heel to be snugly set and further allows the heel to be free from material which may otherwise interfere with the fit of the wearer's shoe. One of the features of the brace is the effect the upper portion of the tear drop slot has in helping the brace to fit snugly without slipping. Because the upper, or superior, portion of the slot is approximately one quarter of an inch above the insertion of the Achilles tendon, and because the area of material 5 above the heel slot has elastic qualities, the brace will fit snugly to the leg and ankle allowing the calcaneal tuberance (heel bone) to secure the proper fitting of the shoe. The result is elimination of slippage of the shoe and pressure or friction points created on the ankle or heel which would otherwise be present if slippage were readily able to occur. The posterior leg section of sleeve 1 has material section 5 between stitching lines 36 that extends from the top of the sleeve 1 to the top of the heel cup slot 27. Material section 5 is made of a stretchable material comprising a thinner and more elastic version of the material making up the sleeve. The thickness of the material can be one thiry-second of an inch or 1-mil and has a weave that is LYCRA or Spandex type and is known commercially as BIOSKIN or EpX. On the dorsal front section of sleeve 1 is material area 6 which is bordered on either side by stitching lines 35. Material 6 is identical to material 5.

Figure 5:
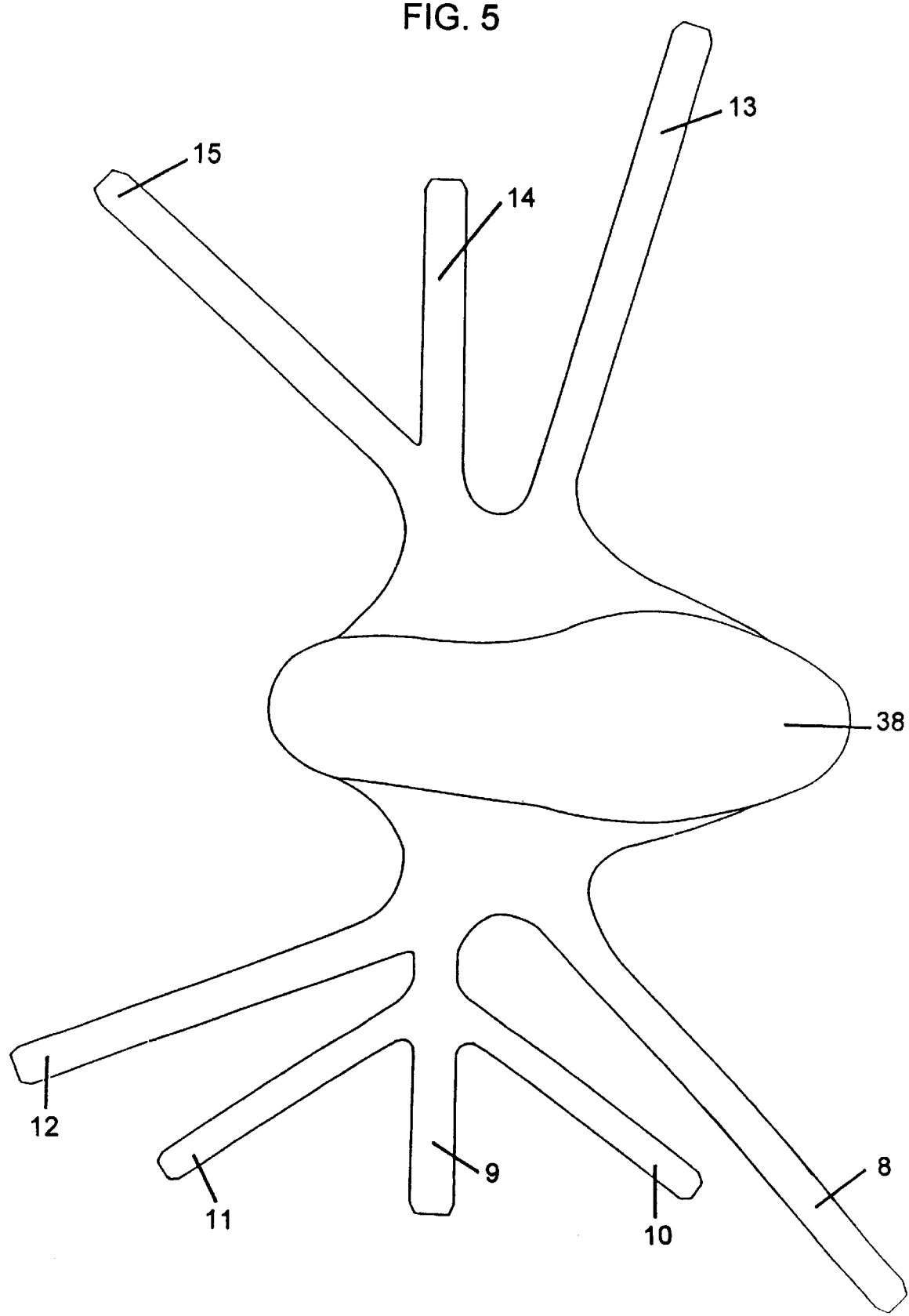
FIG. 5 is a plan view of the mono-unit strapping system.
Figure 6:
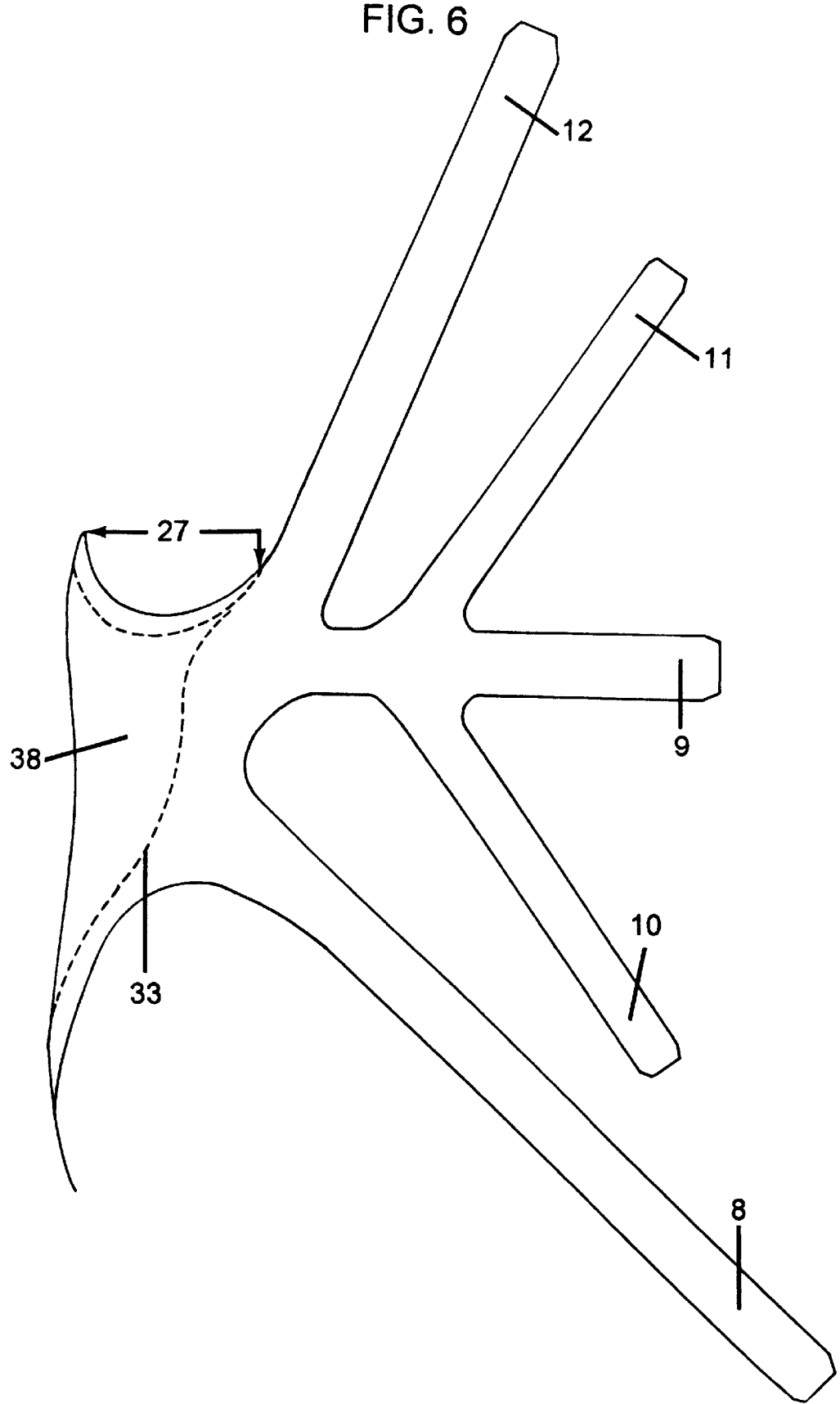
FIG. 6 is a side view of the lateral side of the mono-unit strapping system.
Figure 7:
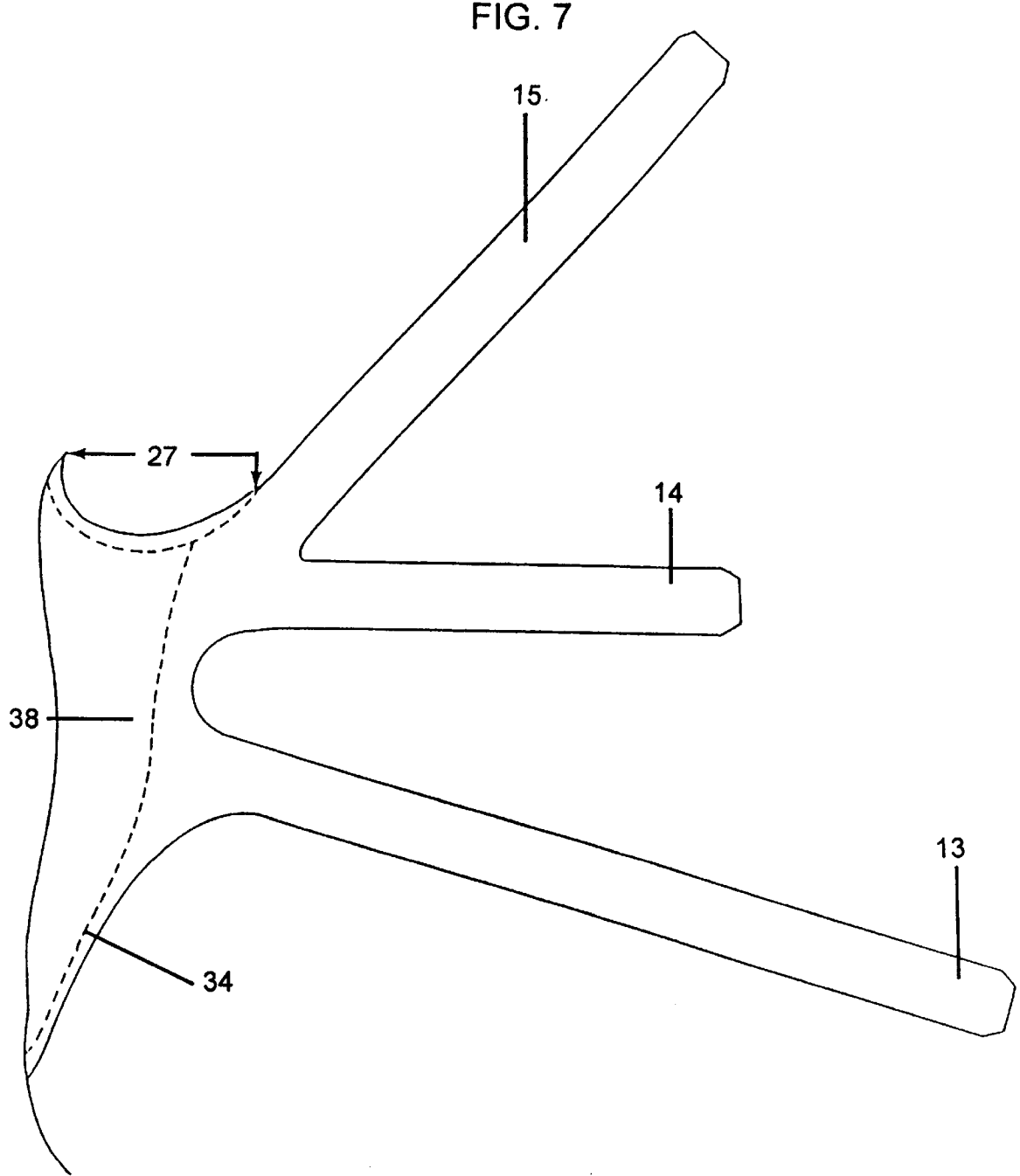
FIG. 7 is a side view of the medial side of the mono-unit strapping system.
Figure 8:
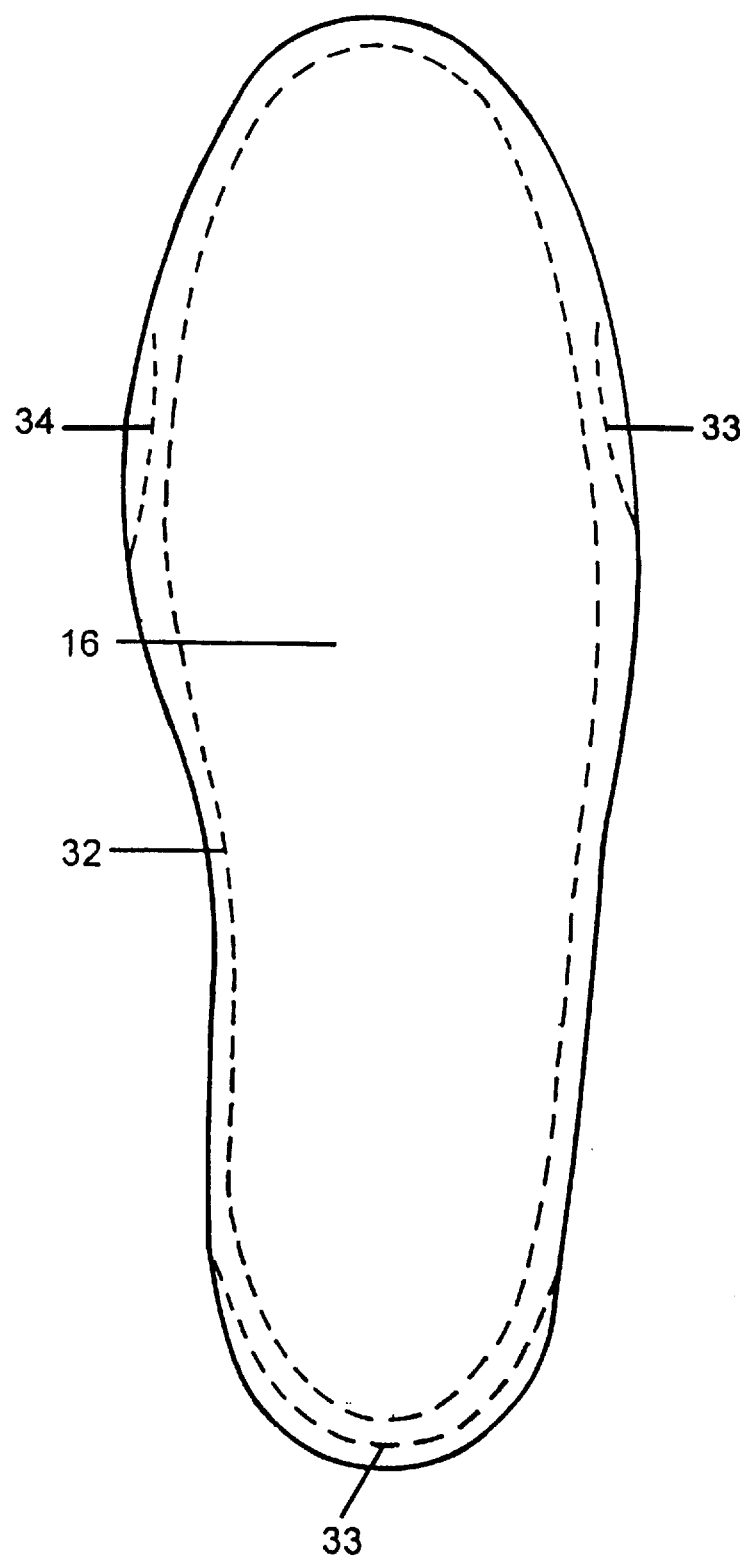
FIG. 8 is a plan view of the plantar area showing the location of stitching.

Turning now to FIGS. 5 through 7, the outer mono-unit bracing system 38 is made of one material. The preferred choice of material is a thermoset or thermoplastic such a KEVLAR. Bracing system 38 includes a plurality of brace straps 8 through 15 each of which are positioned and angled to perform specific support functions mimicking the support provided by tendons and ligaments of the ankle, foot, and lower leg. Lateral stirrup brace strap 9 performs the function of the Calcaneofibular ligament and the Peroneus Brevis and Longus tendons. Strap 9 therefore prevents direct lateral supination or flexion (rolling) of the ankle joint and foot. Stirrup strap 9 further helps lock the Talus bone into the ankle mortise. Strap 9 also includes anterior and posterior lock down straps 10 and 11 respectively. Lock down straps 10 and 11 wrap around the leg to the medial side of the brace and cross over and attach to medial stirrup strap 14. Medial stirrup strap 14 performs the function of the Deltoid ligament which prevents direct medial rolling or flexion of the ankle and also helps lock the talus into the ankle mortise. Lateral figure eight strap 8 is designed to perform the function of the Anterior Talofibular ligament and Extensor Digitorum Longus tendons. Strap 8 helps prevent or reduce the amount of plantar flexion and inversion of the foot. The medial figure eight strap 13 performs the function of the Tibialis Anterior tendon and Deltoid ligament thereby helping to prevent or reduce plantar flexion and eversion of the foot. The lateral heel lock strap 12 performs the function of the Posterior Talofibular ligament and Achilles tendon thereby preventing hyper dorsi-flexion of the ankle joint. Lock strap 12 further helps lock the Talus into the ankle mortise as well as prevent lateral rolling or flexion of the ankle. Medial heel lock strap 15 performs the function of the Deltoid ligament and Achilles tendon helping to lock the talus into the ankle mortise and prevent hyper dorsi-flexion and rolling or flexion of the ankle joint. Both of lock straps 12 and 15 further function the same as the Achilles tendon keeping it from over stretching or rupturing. Stitching lines 33 and 34 located on the lateral and medial sides of bracing system 38 respectively indicate the location along which the outer bracing system 38 fabric is attached to the inner sleeve 1. The anterior sections of stitching lines 33 and 34 angle downward toward the plantar area. FIG. 8 depicts stitching line 32 which is the location along the edges of the plantar surface for attachment of the sleeve 1 and bracing system 38 either directly to or around the plantar cushion 16.

Figure 9:
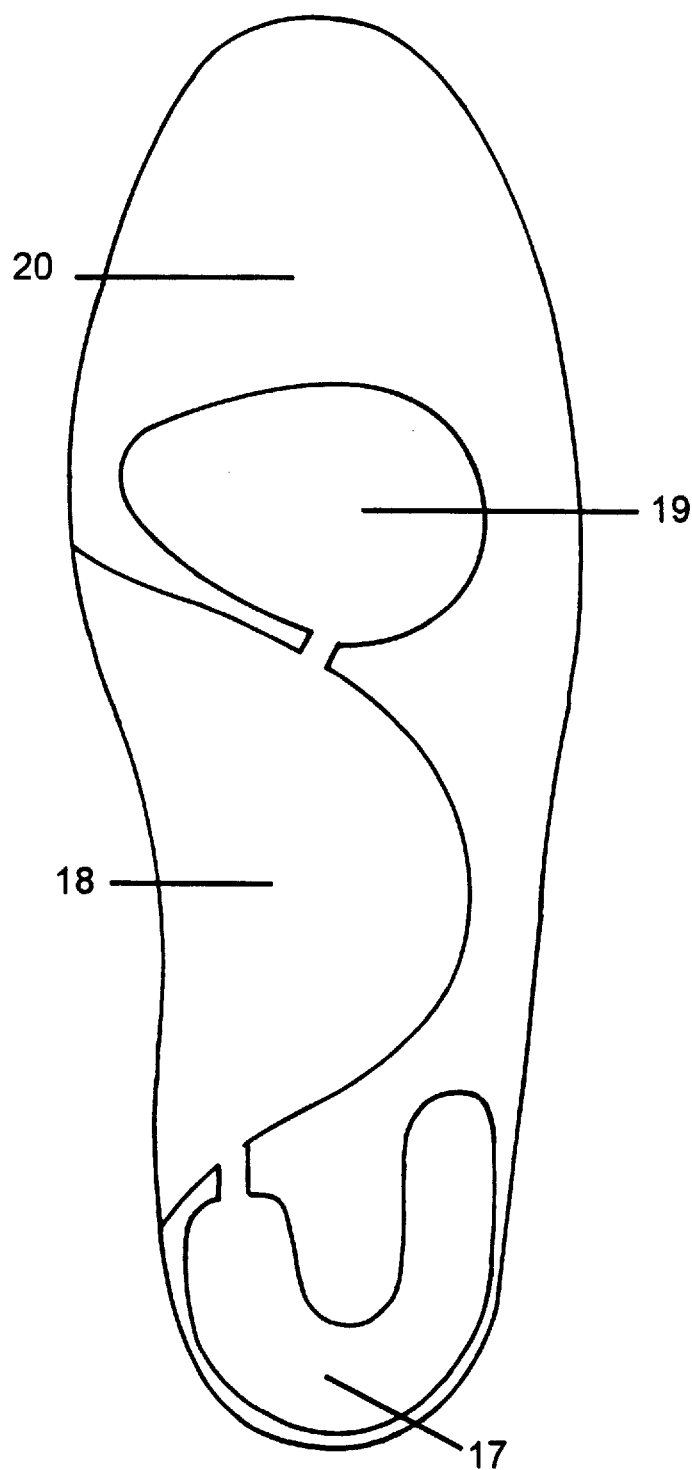
FIG. 9 is a plan view of one embodiment of a plantar cushion showing an outline of the location and shape of a cushion air bladder.
Figure 10:
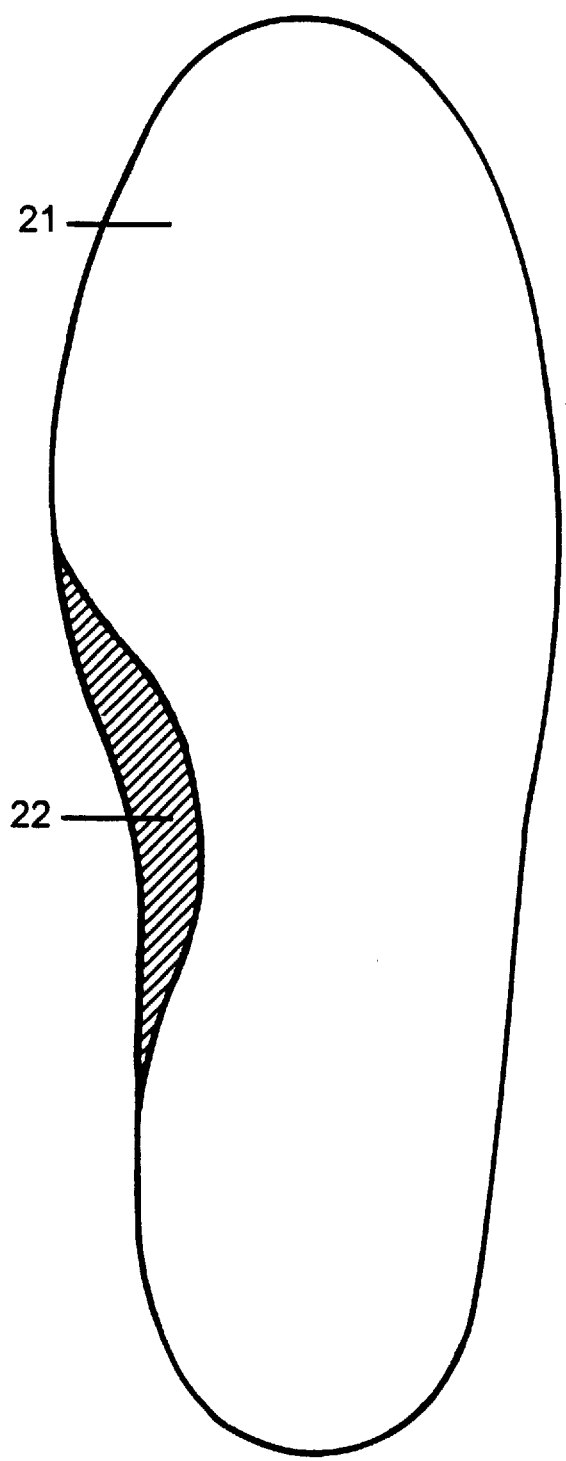
FIG. 10 is a plan view of one embodiment of a plantar cushion having a longitudinal arch support.
Figure 11:
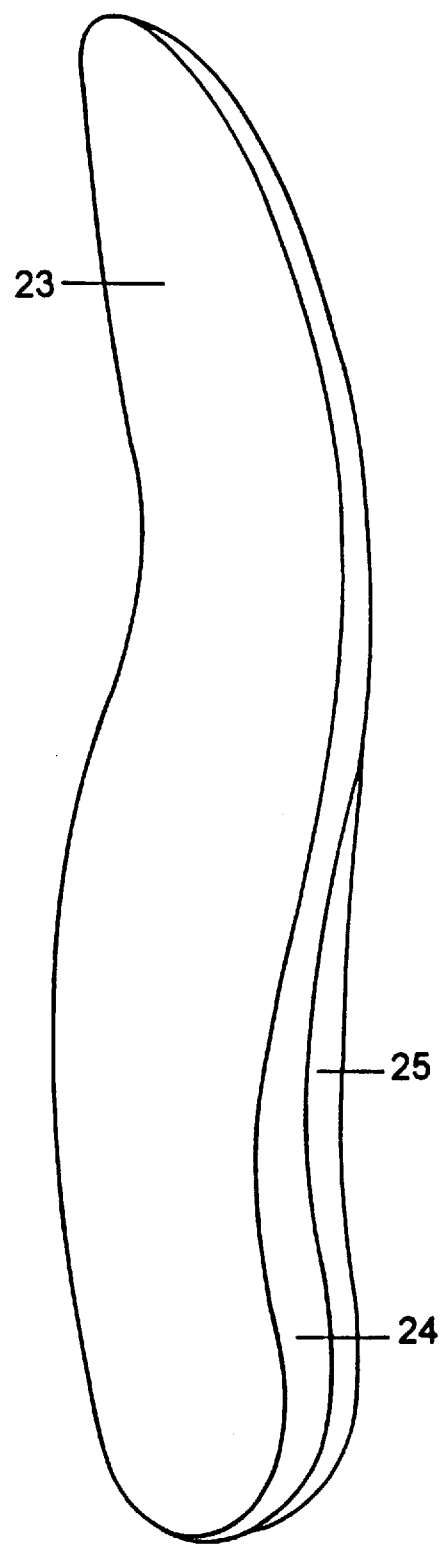
FIG. 11 is a perspective view of one embodiment of a plantar cushion having a multi-component cushion.
Figure 12:
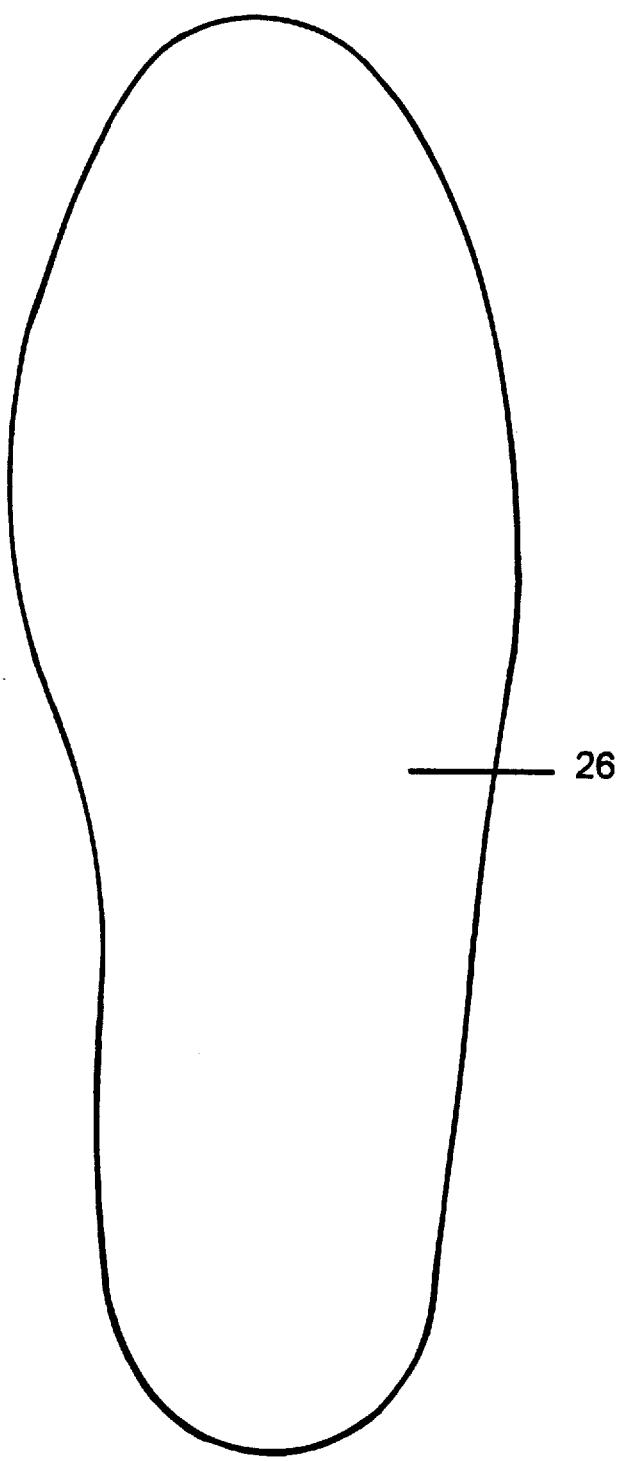
FIG. 12 is a plan view showing the basic pattern of the plantar portion of the brace.
Figure 13:
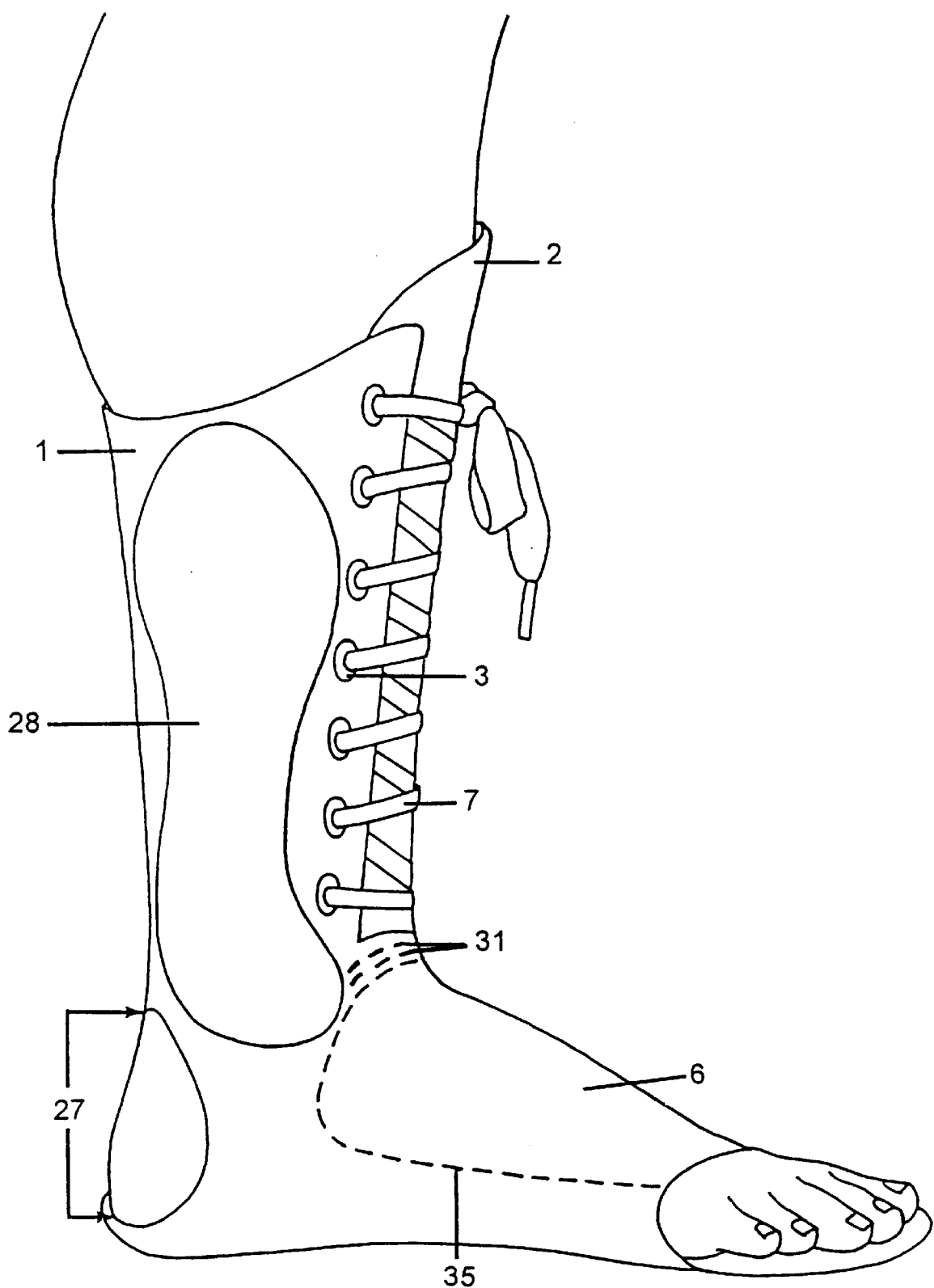
FIG. 13 is a side view showing the lateral aspect of the sleeve and VELCRO attachment.
Figure 14:
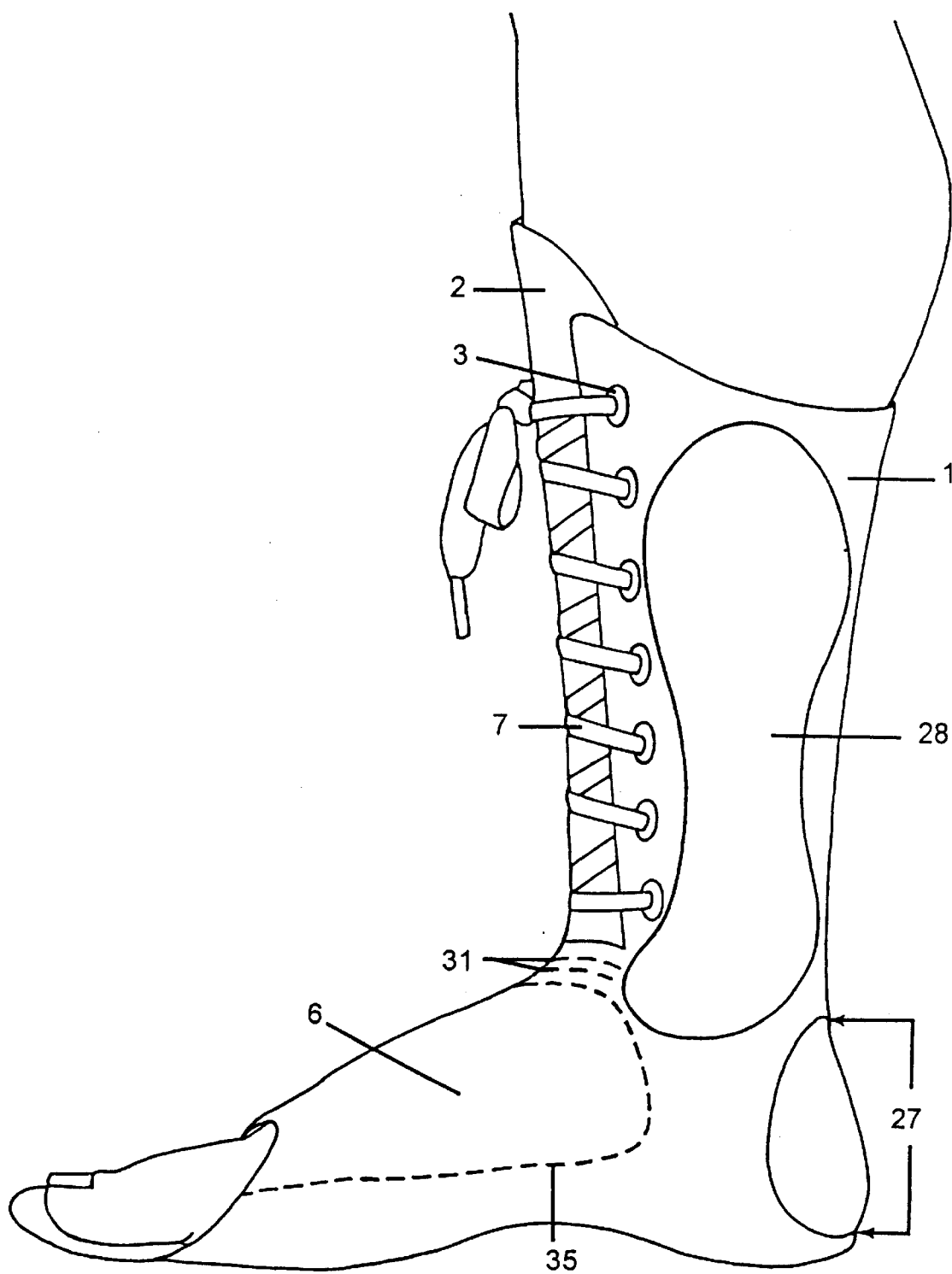
FIG. 14 is a side view showing the medial aspect of the sleeve and VELCRO attachment.

FIGS. 9 through 12 depict various embodiments of the plantar cushion. FIG. 9 contemplates one embodiment of a plantar cushion 20 in the form of an "air orthotic" having an air bladder that includes heel cup bladder 17, arch longitudinal bladder 18 and transverse bladder 19. Another embodiment is demonstrated in FIG. 10 comprising a soft-rigid orthotic plantar cushion 21 having raised arch support 22 which may be customized to the needs of the user. In yet another embodiment, FIG. 11 depicts a bi-density soft-semirigid orthotic plantar cushion 23 made of form fitted foam material 24 which may be hard, medium, or of soft density while shock absorbance material component 25 can be made of more rigid foam or other polymer typically used in the art of shoe sole cushions. Through the use of variable materials, the plantar cushion of the brace can allow for designing a therapeutic orthotic customized to the individual user.

Figure 15:
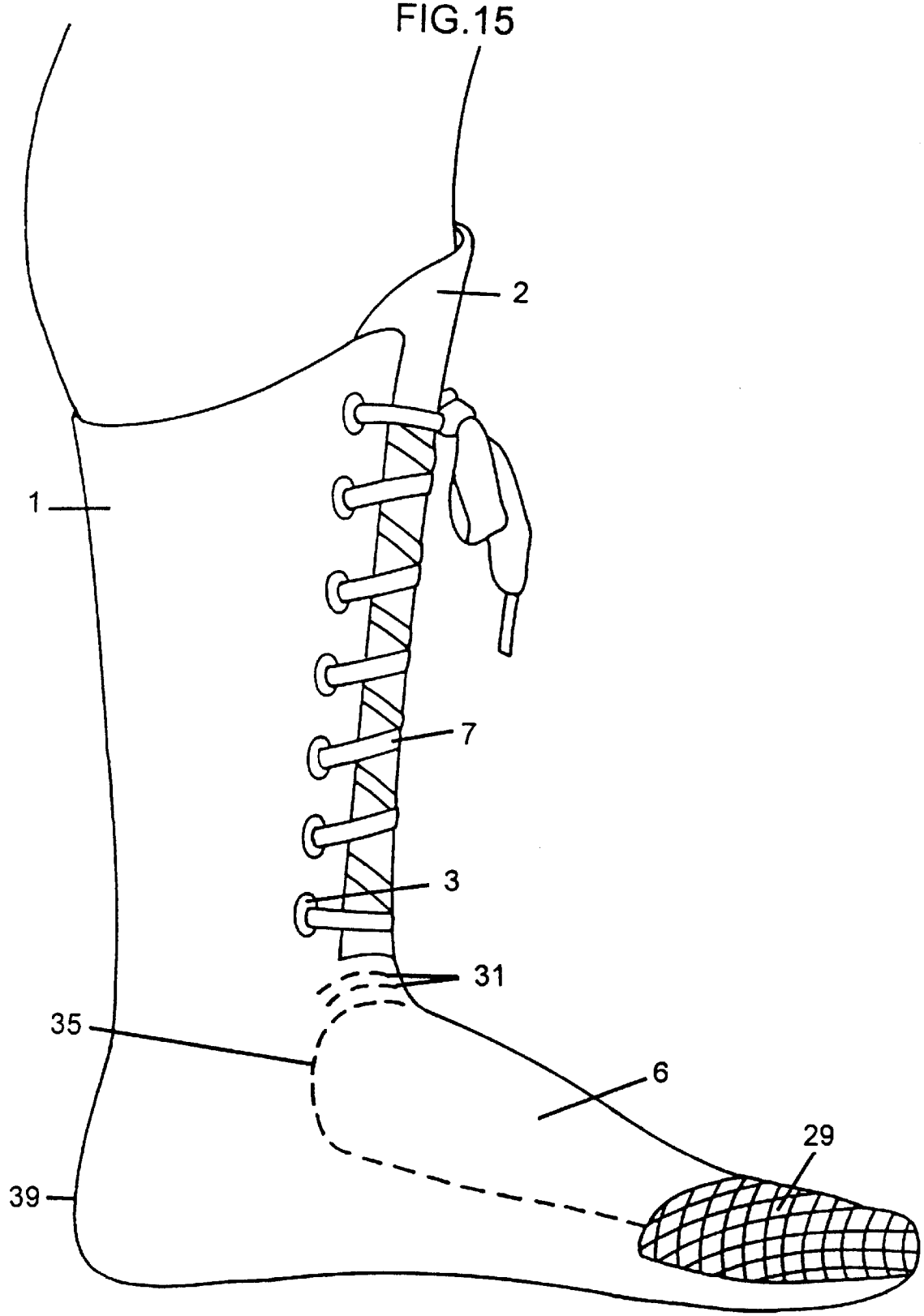
FIG. 15 is a side view showing the sleeve having a covering material over the toe and heel portions of the brace.
Figure 16:
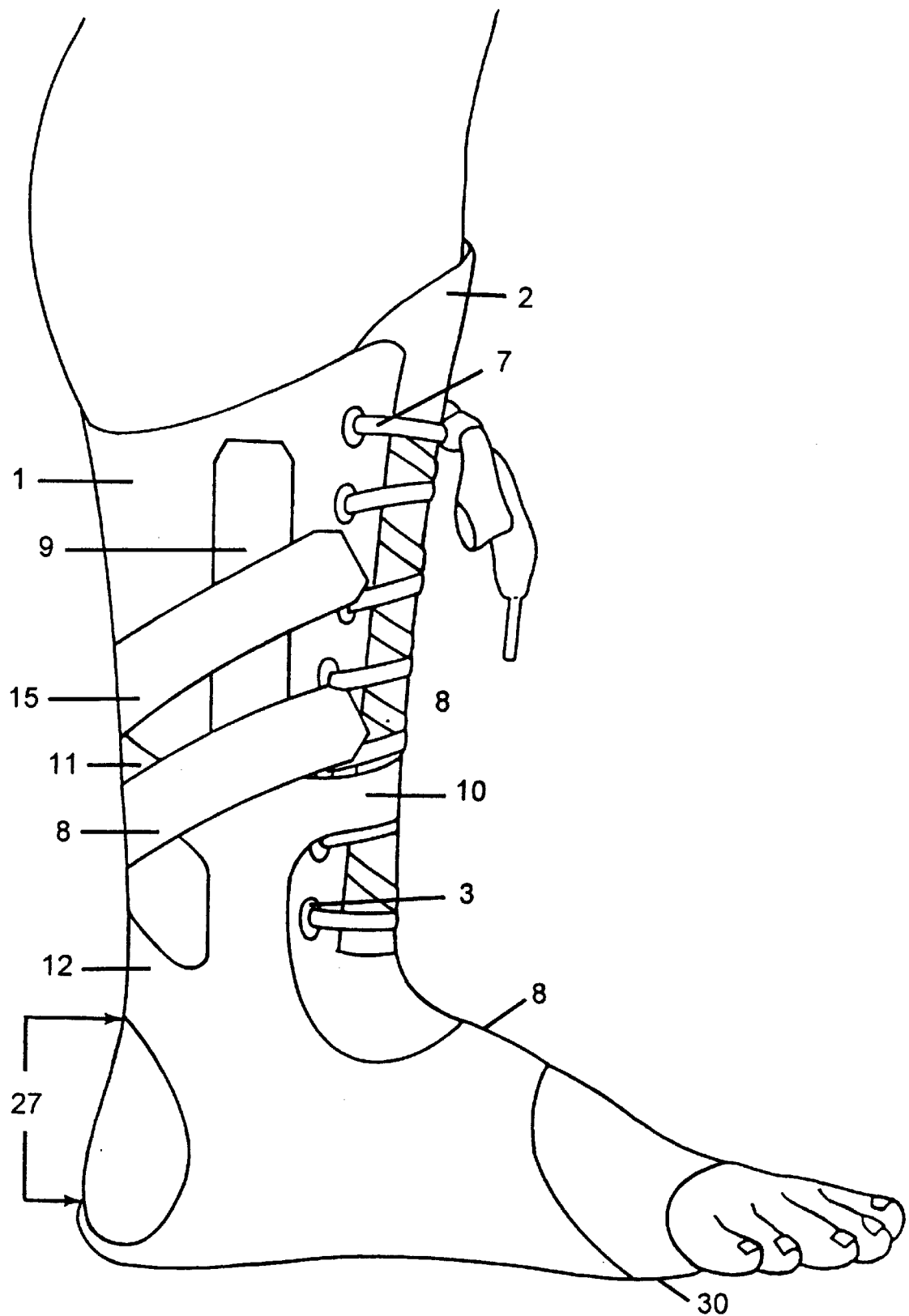
FIG. 16 is a side view showing an embodiment of the complete brace in which the plantar element of the brace extends from the heel up to the base of the toes.
Figure 17:
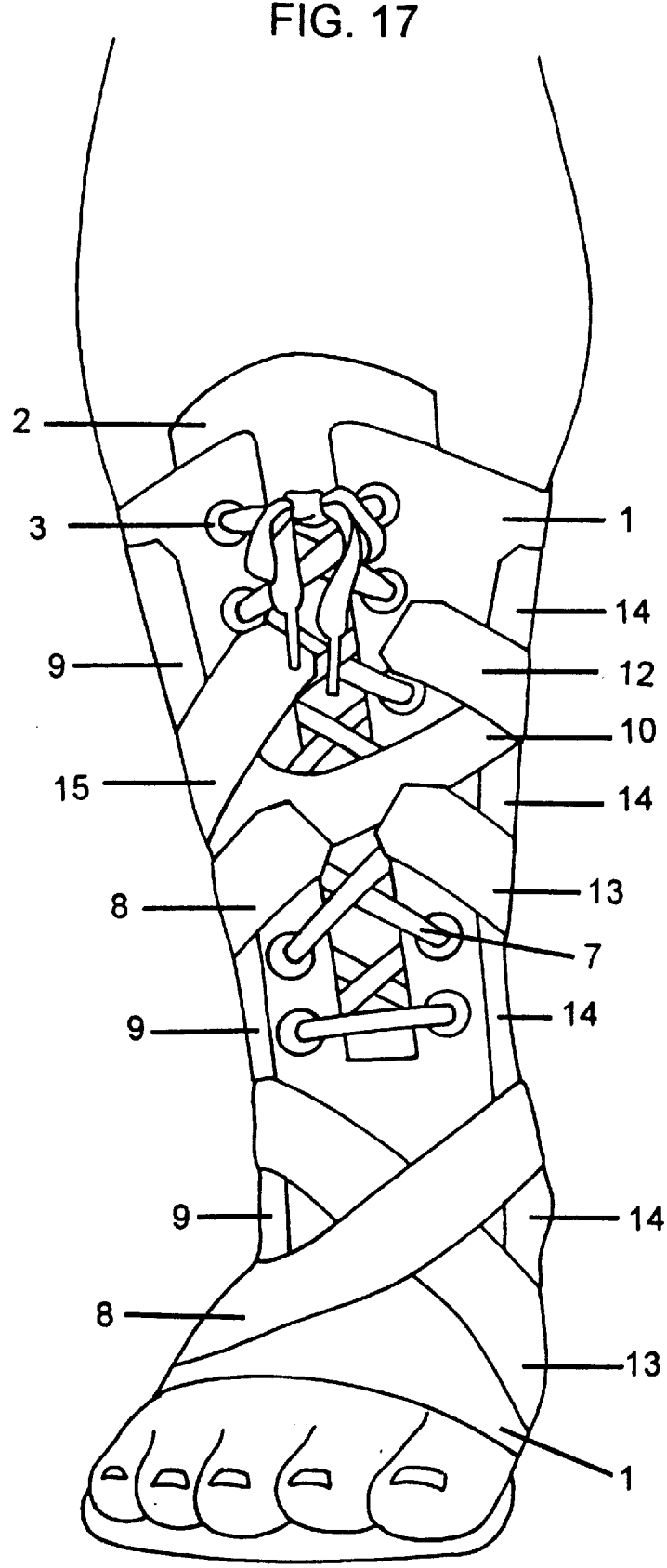
FIG. 17 is a frontal view of the complete brace having a plantar cushion that extends to the distal end of the toes.
Figure 18:
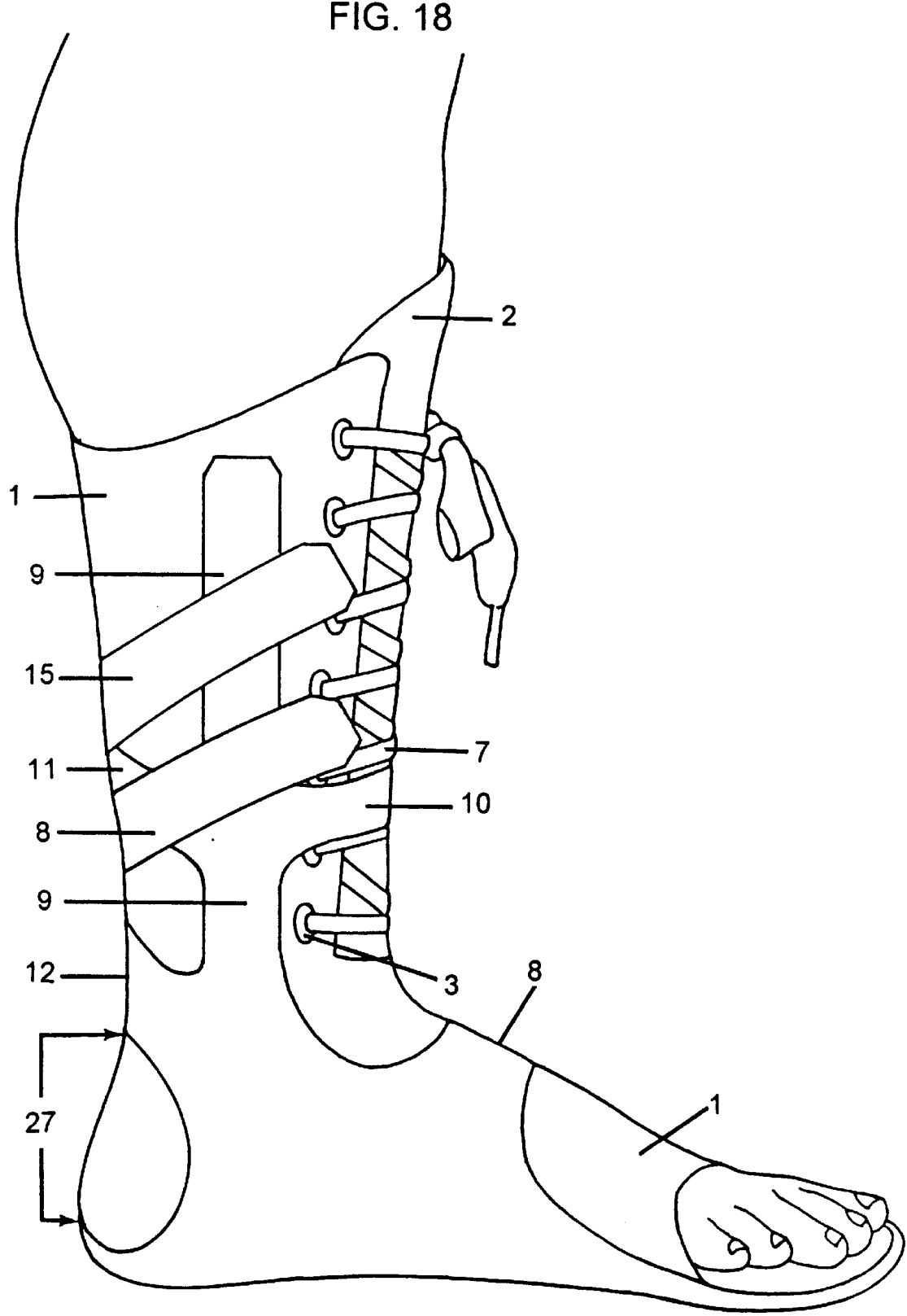
FIG. 18 is a side view showing the lateral aspect of the complete brace having a plantar cushion that extends to the distal ends of the toes.
Figure 19:
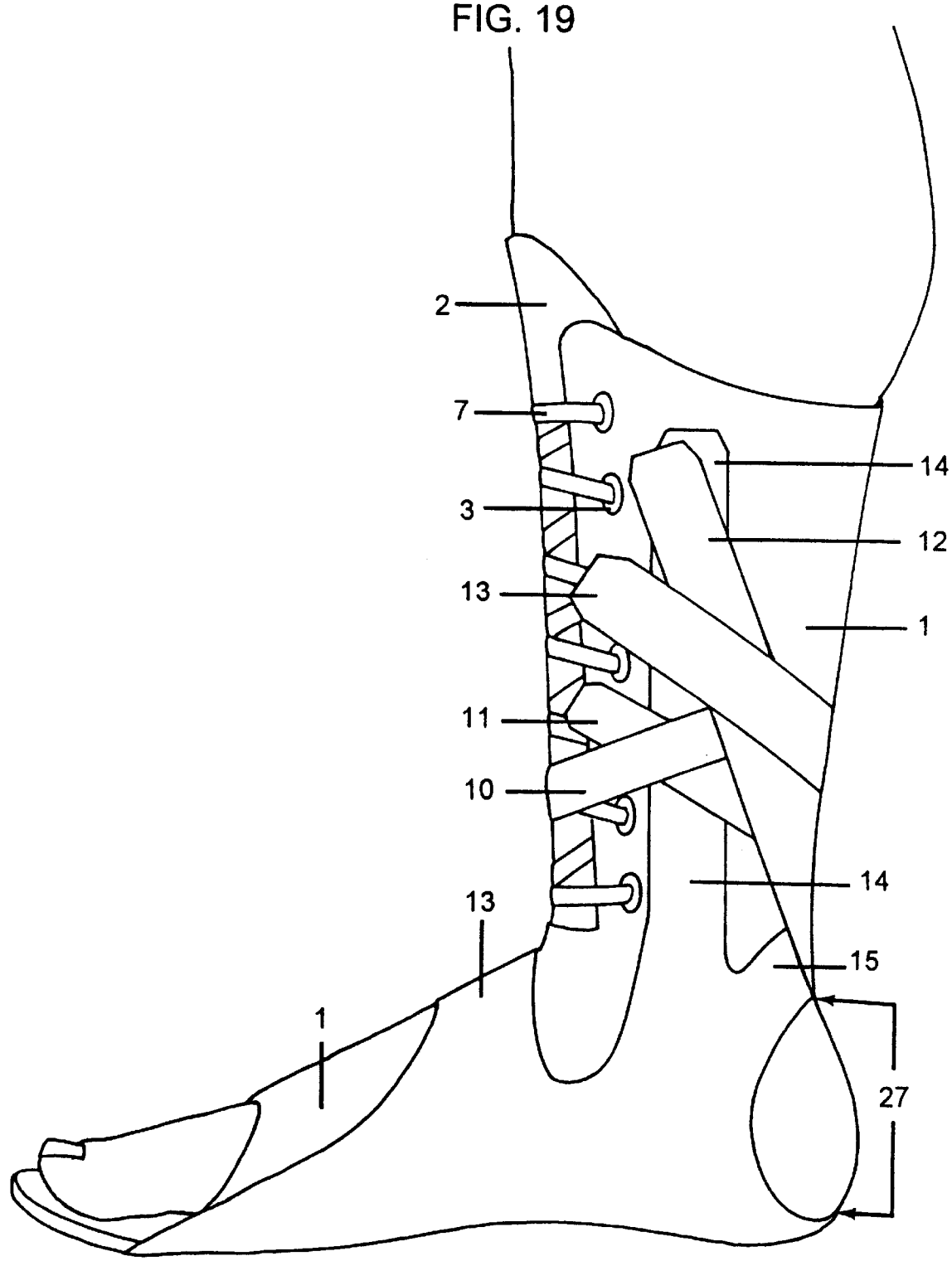
FIG. 19 is a side view showing the medial aspect of the complete brace having a plantar cushion that extends to the distal end of the toes.
Figure 20:
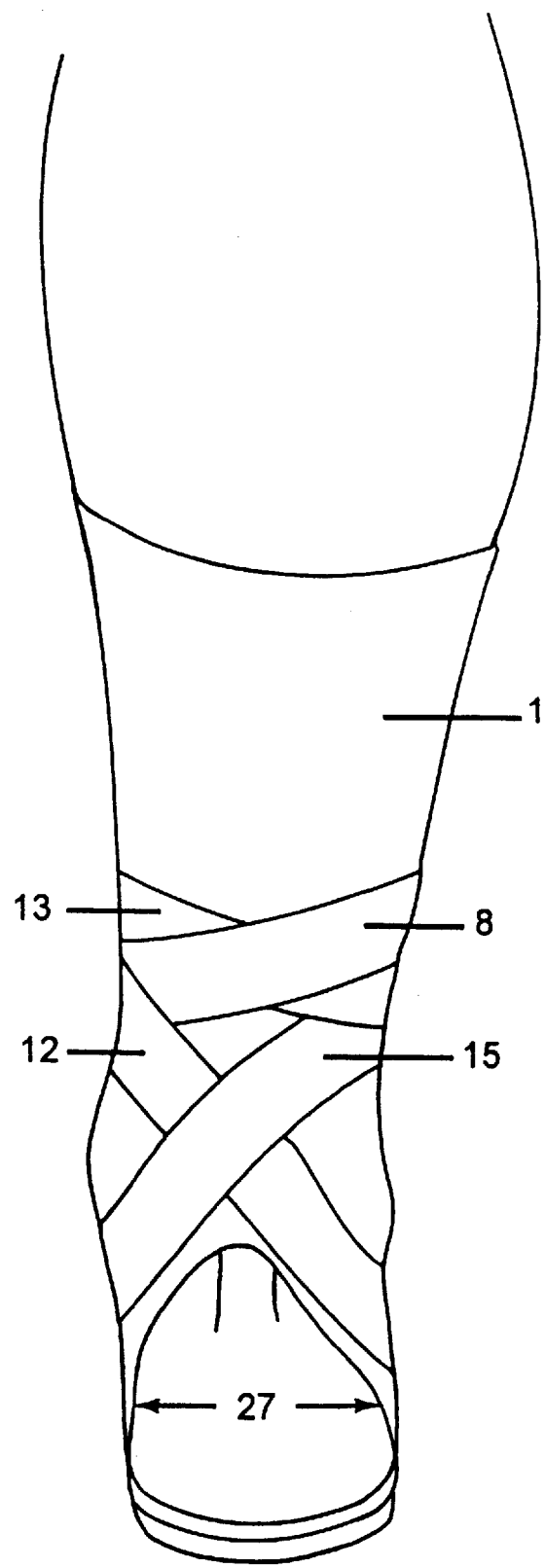
FIG. 20 is a rear view showing the complete brace.

In yet another configuration, FIG. 15 depicts an inner sleeve designed for sport and military use. Here, a breathable mesh covers the toes to make the sleeve more sock like as well as allow the foot to be aerated. The heel area of this embodiment is completely covered by sleeve material 39 such that there is no heel cup slot 27. In this embodiment, the brace is contemplated to be used as a total sock design for situations that will not require any form of orthotic cushion and further allowing for minimal bulk. FIG. 16 shows another configuration in which the sleeve terminates just behind the toes at position 30.

The manner of strapping and means of securing said strapping are depicted in FIGS. 13 through 20. Since the preferred means of securing the straps is VELCRO, sleeve 1 includes VELCRO attachment fabric 28 on both the lateral and medial leg portions of the sleeve 1. Although the manner, order, and degree of tension used for securing the straps may include any number of protocols, generally, lateral stirrup 9 is secured first along with medial stirrup 14. Second, locking straps 10 and 11 are then wrapped and anchored across medial stirrup 14. Third, heel locking straps 12 and 15 are secured. Fourth, figure eight medial strap 13 is wrapped and followed by lateral figure eight strap 8.

While the preferred embodiment of the present invention is shown and described, it is envisioned that those skilled in the art may devise various modifications of the present invention without departing from the spirit and scope of the claims. The invention is not intended to be limited by the foregoing disclosure, but only by the following claims.

We claim:

1. A lower leg, ankle and foot support system for preventing, treating, and rehabilitating injuries to lower leg, ankle joints, and foot musculature comprising:

a) an inner slide-on sleeve;
   b) a plantar cushion; and
   c) an outer mono-unit strapping system;

said inner slide-on sleeve further having a leg, a medial, a lateral, a dorsal arch and a plantar surfaces, said sleeve further having smooth texture across said leg, medial, lateral, dorsal arch and plantar surfaces, said plantar surface further having an outer circumference along which said outer mono-unit strapping system is attached;

said inner slide-on sleeve also having a tongue, and a plurality of shoe lace eyelets, said tongue attached to said sleeve at a position on said sleeve above where the ankle joints of a user would rest when the sleeve is in use, said sleeve further having a shaped top that is higher on an anterior side than on a posterior side of said sleeve such that said shaped top is conformable to muscles of the lower leg when the sleeve is in use;

said plantar cushion having a predetermined shape and elasticity to conform to orthotic requirements of a user, said cushion connected to said sleeve below said plantar surface;

said outer mono-unit strapping system having a central plantar area and a multiplicity of straps, said central plantar area having an outer circumference along which said outer circumference of said plantar surface of said sleeve is attached such that said plantar cushion is in between said plantar surface of said sleeve and said central plantar area of said outer mono-unit strapping system, said multiplicity of straps including a lateral stirrup having anterior and posterior lock straps, a medial stirrup, a lateral anterior figure eight strap, a medial anterior figure eight strap, a posterior lateral heel lock strap, and a posterior medial heel lock strap, said multiplicity of straps having the capacity to tightly secure onto said sleeve.

2. A system according to claim 1 wherein said sleeve has a tear drop shaped opening forming an open heel cup to allow a user's Achilles tendon and calcaneal tuberance to protrude from said sleeve.

3. A system according to claim 1 wherein said plantar cushion, said plantar surface of said sleeve, and said central plantar area of said mono-unit strapping system extends from a posterior heel cup end of said support system to an anterior toe end of said support system such that said anterior toe end is sized and configured to terminate at the base of the user's toes when the sleeve is in use.

4. A system according to claim 1 wherein said slide-on sleeve includes a fabric covering an anterior toe end and a posterior heel cup end of said sleeve.

5. A system according to claim 1 wherein said outer mono-unit strapping system is made of a composite material from the group consisting of thermoplastic, thermoset, a strong resilient thin material, and hook and loop fasteners.

6. A system according to claim 5 wherein said outer mono-unit strapping system is a thickness of about one-thirty-second of an inch to about three-eights of an inch.

7. A system according to claim 1 wherein said slide-on sleeve is made of an elastic resilient composite material.

8. A system according to claim 7 wherein said slide-on sleeve is a thickness of about one-thirty-second of an inch to about three-eights of an inch.

9. A system according to claim 1 wherein said plantar cushion is semi-permanently placed between said plantar surface of said sleeve and said central plantar area of said strapping system.

* * * * *